United States Patent [19]

Goldenberg

[11] Patent Number: 4,932,412

[45] Date of Patent: Jun. 12, 1990

[54] INTRAOPERATIVE AND ENDOSCOPIC TUMOR DETECTION AND THERAPY

[75] Inventor: Milton D. Goldenberg, Short Hills, N.J.

[73] Assignee: Immunomedics, Inc., Warren, N.J.

[21] Appl. No.: 943,561

[22] Filed: Dec. 18, 1986

[51] Int. Cl.$^5$ .............................................. A61B 6/00
[52] U.S. Cl. ................................. 128/654; 128/631
[58] Field of Search ............... 128/1.1, 630, 631, 654, 128/659; 424/1.1, 4, 9

[56] References Cited

U.S. PATENT DOCUMENTS

| | | | |
|---|---|---|---|
| 4,266,549 | 5/1981 | Kimura | 128/654 |
| 4,348,376 | 9/1982 | Goldenberg | 128/659 |
| 4,361,544 | 11/1982 | Goldenberg | 424/9 |
| 4,431,626 | 2/1984 | Henze | 424/9 |
| 4,444,744 | 4/1984 | Goldenberg | 128/659 |
| 4,460,559 | 7/1984 | Goldenberg | 424/9 |
| 4,460,561 | 7/1984 | Goldenberg | 424/9 |
| 4,595,014 | 6/1986 | Barrett et al. | 128/659 |
| 4,624,846 | 11/1986 | Goldenberg et al. | 128/659 |
| 4,782,840 | 11/1988 | Martin, Jr. et al. | 128/654 |

*Primary Examiner*—C. Fred Rosenbaum
*Assistant Examiner*—Sharon Rose
*Attorney, Agent, or Firm*—Foley & Lardner, Schwartz, Jeffery, Schwaab, Mack, Blumenthal & Evans

[57] ABSTRACT

Methods are provided for short-range intraoperative and endoscopic detection and therapy of tumors using radiolabeled antibodies and, in some cases, techniques for reducing or correcting for non-specific background radiation to improve resolution. Therapy using external radiation and/or laser or mechanical endoscopically introduced tumor removal means can be combined with the detection methods to increase precision of the tumor removal operations.

17 Claims, No Drawings

INTRAOPERATIVE AND ENDOSCOPIC TUMOR DETECTION AND THERAPY

BACKGROUND OF THE INVENTION

The present invention relates to improved methods for detecting tumors in the course of intraoperative and endoscopic examination using a small radiation detecting probe, whereby background radiation is reduced, or compensated for, and discrimination between tumor and non-tumor tissue is thereby enhanced.

Surgical resection remains the primary curative approach in the management of cancer. Radioimmunodetection (RAID) is used to locate and stage tumors, and to monitor post-operative patients, typically using serum levels of markers (antigens) produced by and/or associated with tumors ("tumor markers"), e.g., carcinembryonic antigen (CEA), as both a pre-operative diagnostic predicate and a post-operative diagnostic indicator of recurrence. Antibodies and/or antibody fragments which specifically bind tumor markers ("anticancer antibodies") are used as carriers for radiolabels in imaging and for in vitro assays. It will be appreciated that a tumor antigen can serve as a target for an antibody carrier even if it is not present in serum in a detectable amount.

Resolution is affected by several factors that can limit the size of a tumor, especially a metastasis, which can be imaged by RAID. Non-invasive RAID is inherently limited by the distance between the radiation detector and the tumor. In the case of small, deep-seated metastatic tumors, this becomes the limiting factor in their detection.

Second look surgery has been practiced where recurrence of a previously excised primary tumor was indicated by elevated levels of tumor marker, e.g., CEA. Recently, a small gamma detection probe has been developed which is capable of detecting gamma emission at short distances. Its intraoperative use in second look surgery has been reported to provide important information to the surgeon for determining safe margins for resection and for detecting small metastases, by Aitken et al., *Dis. Colon & Rectum*, 27, 279-282(1984).

Nevertheless, elevated background radiation levels can interfere with and vitiate the advantage of short measuring distances in this technique. In addition, non-specific immunoglobulin uptake by tumor tissue can complicate diagnosis. Moreover, background radiation due to non-specific uptake of labeled antibody often increases with time after injection thereof and clearance of non-specific background radioactivity can require several days for optimal detection of tumors. A need therefore continues to exist for methods for reducing background levels and compensating for non-specific immunoglobulin uptake so that enhanced resolution can be achieved for short-range intraoperative and endoscopic tumor detection and therapy.

OBJECTS OF THE INVENTION

The principal object of the present invention is to provide methods for short-range intraoperative and endoscopic detection of tumors whereby discrimination between tumor and non-tumor tissue is enhanced so that smaller tumors can be detected and appropriate margins can be determined more accurately for surgical resection, intraoperative irradiation and/or endoscopic tumor removal.

Upon further study of the specification and appended claims, further objects and advantages of this invention will become apparent to those skilled in the art.

SUMMARY OF THE INVENTION

These objects can be attained, in a method for short-range intraoperative or endoscopic tumor detection, wherein a surgical or endoscopy patient is injected parenterally with a radiolabeled primary antibody which specifically binds a marker produced by or associated with a tumor, the surgically exposed or endoscopically accessed interior of a body cavity of the patient is scanned at close range with a radiation detection probe, and the sites of accretion of the labeled antibody are located by detecting elevated levels of radiation at such sites with the probe; by providing the improvement comprising injecting said patient parenterally, either concurrently or sequentially, with:

(a) a contrast or subtraction agent radiolabeled with a radioisotope emitting at an energy which is separately detectable from the primary antibody label using a radiation detection probe; radiation detected from emission of the contrast or subtraction agent being used to better define the tumor, wherein:

(i) said contrast or subtraction agent comprises an organ, blood pool or interstitial fluid non-tumor-specific contrast agent, and the resultant diffuse distribution of the contrast agent is used to define the organ, blood pool or interstitial region, whereby foci of labeled primary antibody activity are enhanced and better discriminated against a background of reduced diffuse contrast agent label activity; or (ii) said contrast or subtraction agent is a dual isotope correction agent comprising irrelevant immunoglobulin from the same or different species as that used to prepare the primary antibody, the irrelevant immunoglobulin being so labeled that the kinetics and distribution of the radiolabeled primary antibody and irrelevant immunoglobulin in the patient are substantially the same during the time period required for scanning; and wherein the ratio of primary antibody label activity to irrelevant immunoglobulin label activity at a selected site is compared to said ratio at a known non-tumor site, whereby an elevated level of primary antibody label accretion due to antigen-antibody complex formation at said selected site can be discriminated;

(b) unlabeled second antibody which specifically binds the primary antibody or the labeling moiety thereof, the second antibody being injected at a time after the injection of the primary antibody sufficient to permit specific uptake of the primary antibody by a tumor in the body cavity, and in an amount sufficent to reduce the circulating level of the primary antibody label by at least about 10-85%, or to increase the localization ratio of the labeled primary antibody by at least about 20%, within about 2-72 hours following injection of the second antibody, whereby background levels of nonspecifically distributed primary antibody and/or label are reduced in the body cavity, and the sites of accretion of labeled primary antibody as well as the level of specific uptake thereof are more effectively discriminated.

In a related aspect, the invention provides a method for short-range endoscopic tumor detection, comprising injecting an endoscopy patient parenterally with a radiolabeled primary antibody which specifically binds a marker produced by or associated with a tumor, scanning the endoscopically accessed interior of a body cavity of said patient at close range with a radiation detection probe, and locating the sites of accretion of said labeled antibody by detecting elevated levels of radiation at said sites with said probe.

Thus, the use of endoscopic detection, in combination with radiolabeled antibodies, to detect and define tumors and tumor margins represents a novel technique in its own right, even without the improved background correction and/or reduction methods described herein with respect to surgical techniques where the patient is operated upon to open and expose an area of possible tumor growth. The further combination of such endoscopic detection with background correction or reduction techniques and/or with means for coagulating and/or removing tumor tissue and immediately adjacent tumor margins through the endoscope represent embodiments which improve upon this basic aspect of the present invention.

The technique of injecting labeled specific antibody and separately detectably labeled irrelevant antibody for non-specific background correction is referred to herein, interchangeably, as "subtraction" or "dual isotope correction".

Combinations of the foregoing methods can also be used to further enhance the resolution of the tumor detection process. For example, subtraction can be combined with second antibody clearance to produce even greater differentiation between specific uptake of labeled antibody and background due to circulating labeled antibody, free label and/or non-specific uptake of immunoglobulin and/or label. Hybrid antibodies which specifically bind both primary antibody and label can be used to clear background label regardless of whether the integrity of the antibody conjugate is maintained or whether the label has become detached from the antibody or antibody has metabolized, fragmented or has otherwise been degraded. In this context, the term "label" refers to whatever carrier for the label is used to bind the radionuclide to the antibody, e.g., a chelator for a radiometal ion, a metabolite and/or fragment of the antibody bearing the radionuclide, e.g., a tyrosine residue substituted with one or more atoms of a radioactive iodine isotope, whether as such or incorporated in a longer oligopeptide or further metabolized, or a radioiodide ion or other iodinated species, or the like.

DETAILED DISCUSSION

It must be recognized that the present method relates to intraoperative or endoscopic examination of tissues and/or organs with a radiation detector capable of close approach to suspected sites of tumor recurrence, metastasis or incomplete removal, rather than a non-invasive tumor imaging procedure. Subtraction methods, as hitherto practiced, rely on normalizing counts emitted from two different radionuclides having two different energy ranges. The counts are accumulated, generally over a time of less than one hour to several hours, by scanning a selected body region, using a gamma camera equipped with a suitable collimator. The counts are then normalized, pixel-by-pixel, after which the processor constructs an image by first subtracting the counts calculated to correspond to background from the specific label counts for each pixel, and then displays the result, e.g., as a graded color or black and white image.

In contrast to the foregoing techniques, the method of the present invention does not involve processing of images, both target specific and non-target specific. Rather, it enables a surgeon or clinician, through the use of an intraoperative probe or an endoscope, to scan areas of suspected tumor growth relatively quickly and use the level of counts, or the differences in counts in selected scan sites and the ratio of tumor to non-tumor counts, to more precisely discriminate tumor tissue from non-tumor tissue and thereby more precisely define tumor borders for surgical resection or diagnostic evaluation, or for external radiation therapy.

Earlier workers have indicated the desirability of reducing background counts in an intraoperative probe method without suggesting how this can be achieved. The present method provides solutions to this problem. By reducing non-target radioactivity, either directly or by compensating for it so that it can be effectively factored out, and thereby increasing the ratio of counts due to specific uptake to those due to background, a better discrimination can be achieved, to permit improved demarcation of tumor sites and borders.

The invention also embraces embodiments wherein optimal times for surgery and intraoperative radiodetection and radiotherapy are indicated. Both subtraction methods and second antibody clearance for enhanced imaging can optimize images using repeated scans at different intervals following injection of primary antibody and/or second antibody. On the other hand, for a surgical procedure, it will be necessary to optimize the injections of primary and/or second antibody to coincide with the surgical schedule. By taking a blood sample at intervals after injection of second antibody, the concentration of radioactivity in the circulation can serve as an indicator of the best time for surgery and intraoperative radiation detection, and/or whether a repeated dose of second antibody is indicated.

Use of a radionuclide label with both therapeutic and diagnostic emissions permits further refinement in the foregoing techniques. For example, an antibody labeled with Cu-67, having both beta and gamma emission of appropriate energies, permits the surgeon to detect and excise foci of high activity, using primarily the gamma emission, and at the same time to permit areas of slightly elevated activity to benefit from the therapeutic, i.e., cytotoxic to tumor cells, radiation, primarily the beta emission, or to target these areas for external radiation treatment.

The short-range tumor detection method according to the invention uses a detector capable of detecting radiation emitted from a radiolabel bound to the primary antibody. The radiation can be alpha, gamma, beta, positron or any other detectable radiation which can be produced by a convenient label capable of attachment to an antibody. For example, a gamma detector suitable for such a function has been reported by Aitken et al., *Dis. Colon & Rectum*, 27, 279–282(1984). These authors describe a hand-held gamma probe using a cadmium telluride scintillation crystal, a preamplifier and an amplifier with a digital readout displaying the radioactive counts (Radiation Monitoring Devices, Watertown, Mass.). The scintillation crystal is housed in a 16-mm diameter lead collimator with a 4-mm aperture. This device has been shown to detect tumor with radiolabeled antibody injected intraperitoneally, and to distinguish tumor tissue from nearby non-tumor tissue. No subtraction or enhanced clearance was used or suggested by these authors, nor was any use outside other than in a surgical procedure suggested. Further, the method requires long delays between injection and probing, with unpredictable results obtained from patient to patient.

It will be apparent to the ordinary skilled artisan that other such detectors can be used and that the detector is not limited to gamma radiation. It will also be apparent that the detector can be made to discriminate between different energies of incident radiation, e.g., between gamma radiation in different ranges within the broad 50–500 KeV range which is normally used for gamma scintillation counters and/or between alpha, gamma and beta radiation emitted by labels on the specific and the indifferent antibodies. Thus, the invention is not limited by the type of detector used, but is generally applicable to reducing background radiation levels regardless of the type of radiation used for detection or radionuclide(s) used to label the primary antibody and/or the irrelevant antibody, organ, blood pool or interstitial subtraction agent.

The detector(s) must be able to distinguish between the radiation emitted by the primary antibody label and that emitted by the subtraction agent, in those cases where dual antibody correction is used to enhance sensitivity. This can be effected by using two different probes or by using a single probe which is programmed to record counts of different energies in different channels, or to distinguish by other electronic means between radiation of different types or energies. One way in which this can be accomplished is to detect differences in brightness of a scintillation crystal response, which correlates with differences in photon energy of impinging gamma radiation, using a photomultiplier and a comparator circuit. The circuit is present to respond only to levels above a selected level corresponding to the desired gamma energy band for one of the two radioisotopes.

A scintillation crystal can be mounted on the end of a fiber optic cable and its optical response to incident gamma radiation can be transmitted to a photomultiplier and associated circuitry through the optical fiber. This can reduce the size of the detector to be compatible with use in conjunction with an endoscope (broadly defined). The endoscope can be shielded to serve as a collimator, where necessary, and/or fitted with a window at a known distance from its terminus, with the scintillation crystal housed therein. Various other modifications and adaptations of the foregoing will be readily apparent to the ordinary skilled artisan, in light of the particular needs of the situation. However, the method of the present invention is not limited by any specific type of radiation detector. Rather, any detector which is capable of detecting radiation emitted by an antibody label localized in tumor tissue can be used.

The probe can be used in the form of an endoscope, and inserted into a body cavity through an orifice, such as the mouth, nose, ear, anus or vagina. The term endoscope is herein used generically to refer to an anally introduced endoscope, an orally introduced bronchoscope, a urethrally introduced cystoscope, or the like. Certain of these may benefit greatly from further progress in miniaturization of components and their utility to practice the method of the present invention will be enhanced as a function of the development of suitably microminiaturized components for this type of instrumentation. Highly miniaturized probes which could be introduced invascularly, e.g., via catheters or the like, are also suitable for use in the method of the invention.

The radionuclide label used for detection agents according to the method of the present invention is preferably an isotope with a gamma radiation emission peak in the range of 50–500 Kev, primarily because he state of the art for radiation detectors currently favors such labels. Suitable such radionuclides include, e.g., Iodine-131, Iodine-123, Iodine-126, Iodine-133, Bromine-77, Indium-111, Indium-113 m, Copper-67, Gallium-67, Gallium-68, Ruthenium-95, Ruthenium-97, Ruthenium-103, Ruthenium-105, Mercury-197, Mercury-203, Rhodium-99 m, Rhodium-101, Rhodium-105, Tellurium-121 m, Tellurium-122 m, Tellurium-125 m, Thulium-165, Thulium-167, Thulium-168, Rhenium-186, Technetium-99 m Fluorine-18. Preferred radionuclides are Iodine-131, Iodine-123, Technetium-99 m, Indium-111 and Gallium-67. Preferred gamma emitters include Iodine-131, Iodine-123, Indium-111, Gallium-67 and Technetium-99 m.

Where more than one isotope is used for a method involving dual isotope correction, the two labels should be of sufficiently different energies to be separately detectable with the probe. Suitable such pairs of radioisotopes include, e.g., Iodine-131/Iodine 123, Gallium-67/Indium-111, Iodine-131/Technetium-99 m and the like. It will generally be preferable that paired radionuclides used for subtraction should not both have significant scatter into channels wherein the emission of the other nuclide is being detected. A one-way scatter can readily be corrected for with currently available probe software.

In one embodiment of the present invention, techniques useful for subtraction in imaging applications are adapted to intraoperative detection. Methods of localization and therapy of tumors and infectious lesions, and methods of organ imaging, using labeled antibodies and antibody fragments which specifically bind markers produced by or associated with tumors, infectious lesions and normal organs or tissues, have been disclosed, inter alia, in U.S. Pat. Nos. 4,331,647, 4,348,376, 4,361,544, 4,444,744, 4,460,561 and 4,624,846, and in related pending applications U.S. Ser. Nos. 609,607 and 751,877, the disclosures of all of which are incorporated herein in their entireties by reference (hereinafter, "the Goldenberg patents"). These references also disclose antibodies and antibody fragments for use in the foregoing methods, together with methods for obtaining them and for labeling them with appropriate radionuclides.

The antibody used as the primary imaging agent in the method of the present invention may be whole IgG, IgA, IgD, IgE, IgM and the like, or a fragment such as, e.g., F(ab')2, F(ab)2, Fab', Fab or the like, including isotypes and subtypes thereof. It can be a polyclonal antibody, preferably an affinity-purified antibody from a human or an appropriate animal, e.g., a primate, goat, rabbit, mouse or the like, or a monoclonal antibody prepared by conventional techniques, e.g., a murine antibody derived from a hybridoma produced by fusion of lymph or spleen cells from a mouse immunized against a cancer antigen with myeloma cells from an appropriate immortal cell line. It will be appreciated that newer techniques for production of monoclonals can also be used, e.g., human monoclonals, interspecies monoclonals, chimeric (e.g., human/mouse) monoclonals, genetically engineered antibodies and the like.

It should be noted that mixtures of antibodies, isotypes, and immunoglobulin classes, including fragments, can be used, as can hybrid antibodies and/or antibody fragments. The hybrids can have two different antigen specificities, e.g., one arm binding to a tumor antigen such as CEA and another arm binding to another antigen, e.g., CSAp. Or one arm could bind to one epitope on, e.g., CEA and the other arm could bind to another CEA epitope. The foregoing are merely illustrative, and other combinations of specificities can be envisioned that also fall within the scope of the invention. Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., *Immunol. Today*, 5, 299(1984).

Organ-specific and/or blood pool subtraction agents are used in the present method to aid in evaluating and compensating for non-specific antibody uptake in and around tumor tissue. Suitable such agents are disclosed, inter alia, in the Goldenberg patents incorporated by reference herein, more particularly in U.S. patent application Ser. No. 751,877. These include, but are not limited to, radiolabeled antibodies to markers characteristic of lymphatic tissue, organs such as liver, spleen, pancreas, and the like. Many antibodies which specifically bind to tissues of these organs are known and/or under current investigation and development.

Organ-associated and organ-specific antibodies can be developed by immunizing a suitable animal host with certain mammalian tumors or normal organ/tissue extracts and/or cells. It is well known that use of tumors as immunogens can result in antibodies which not only react with neoplasia but also with normal tissue components which sometimes show an organ-restricted nature. Histogenetic and functional differences between various tissues and organs of the body of course suggest that distinct antigens are present and identifiable. A body of scientific literature already exists which claims the identification of organ-specific antigens, either using classical immunization approaches or by immunizing with specific tumors, and this is reviewed by Goldenberg et al., *Cancer Res.*, 36, 3455(1976), showing that such antigens are known and available.

Similar organ- and tissue-associated and specific antigens are identifiable by hybridoma methods which produce monoclonal antibodies. One recent development is the production of human hybridoma monoclonal antibodies by securing lymphocytes or plasma cells from patients showing certain organ-restricted autoimmune diseases, e.g., thyroiditis, gastritis, ulcerative colitis, myositis, and the like. These antibody-producing cells are then fused in vitro with human or murine myeloma cells and hybridomas capable of generating appropriate anti-organ and anti-tissue antibodies are produced and propagated, using wellknown methods. Also, patients with specific tumor types can be used as a source of such lymphocytes or plasma cells, or such patients can be further immunized with such tumor cells for stimulating the production of anti-organ and anti-tissue antibodies. The lymphatic tissue removed is then used for fusion with suitable myeloma cells, by procedures which are by now widely known and conventional in the art.

Organ associated and organ-specific antigens can be isolated for immunization of another species, e.g., subhuman primates, rodents, rabbits, goats, etc., by a number of methods known in the art, such as isolation of cell membranes or disruption of the cells, e.g., by centrifugation, sonication, etc., to obtain intracellular antigens. It is preferable, for these purposes, to use intracellular as opposed to surface and extracellular antigens. In this manner, organ-associated and organ-specific antigens can be obtained from a large number of tissues and organs of the body, including brain, thyroid, parathyroid, larynx, salivary glands, esophagus, bronchus and lungs, heart, liver, pancreas, stomach and intestines, kidney, adrenal gland, ovary, testis, uterus, prostate, etc. Of further interest is the differentiation of different tissue and cellular components within an organ, such as tubular and glomerular kidney, different regions and cell types of the brain, endocrine and exocrine pancreas, etc., especially by the identification of antigens and antigen epitopes restricted to the individual cell and tissue types in question, as accomplished with polyclonal and/or hybridoma-monoclonal antibody-production methods known in the art.

Examples of antibodies which specifically bind to lymphatic cells and/or tissues include, but are not limited to, the T101 murine monoclonal anti-T-cell antibody reported by Royston et al., *Blood*, 54(*Suppl.* 1), 106a(1979); and the T200 anti-lymphoreticular cell monoclonal antibody whose specificity was reported by Hsu et al., *Am. J. Pathol.*, 114, 387(1984). Other antibodies to T-cells and B-cells, which can also be used for such agents, include, e.g., the B1, B2 and BA1 anti-B-cell monoclonal antibodies reported in Hsu et al., *Am. J. Clin. Pathol.*, 80, 415(1983), and in Hsu et al., *Am. J. Pathol.*, 114, 387(1984); the OKT10, A1G3, HLA-DR and Leu 10 monoclonals reported in Hsu et al., Ibid.; and anti-lymphocyte monoclonals reported by Foon et al., *Blood*, 60, 1(1982), LeBien et al., *J. Immunol.*, 125, 2208(1980), and Beverley et al., *Eur. J. Immunol.*, 11, 329(1981).

Again, the antibody may be whole IgG, IgA, IgD, IgE, IgM and the like, or a fragment such as, e.g., F(ab')2, F(ab)2, Fab', Fab or the like, including isotypes and subtypes thereof. It can be a polyclonal or a monoclonal antibody, preferably an affinity-purified polyclonal antibody or a monoclonal antibody prepared as described hereinabove for primary antibodies, including chimeric, genetically engineered, human, interspecies and the like. Again, mixtures of antibodies, isotypes, and immunoglobulin classes, including fragments, can be used, as can hybrid antibodies and/or antibody fragments. In particular, hybrids having both T101 and T200 specificities, or hybrids having anti-T-cell and anti-B-cell specificities, may be especially useful as lymphatic organ subtraction agents when lymph node metastases are being sought.

Radiocolloids can also be used as organ-specific subtraction agents since they accrete in the lymphatic system and also are scavenged by the reticuloendothelial system (RES) and are cleared to the liver and spleen. Examples of such radiocolloids include, but are not limited to, e.g., Tc-99-antimony sulfur colloid (Tc-ASC), Tc-99 sulfur colloid, Tc-99 stannous phytate, Au-198 colloid, Hg-197 sulfide colloid, In-111 phosphate colloid and the like, as well as other types of agents, e.g., radiolabeled liposomes, reported in the literature. Other colloidal preparations using radionuclides other than Tc or Au can be used, e.g., colloidal In-111, Ru-97, Ga-67, and the like, or colloids incorporating I-131 or I-123. Such preparations are conventional and well known to the ordinary skilled artisan in this field. See, e.g., Rayudu, "Radiotracers for Medical Applications, Vol. I" (CRC Press, Boca Raton, Fla., 1983).

Suitable blood pool and interstitial subtraction agents include, but are not limited to, radiolabeled salts, e.g., 99 m-TcO4-, radiolabeled soluble proteins, e.g., 99 m-Tc-human serum albumin (HSA), radiolabeled blood cells, e.g., 99 m-Tc red blood cells (RBC's), 111-In white blood cells (WBC's) and the like.

The subtraction agent, here used as an organ, blood pool or interstitial fluid contrast agent, defines the organ, blood pool region or interstitial region with a diffusely distributed area of radioactivity. Foci of accretion of the specific label are detected as enhanced areas against a background of reduced diffuse label of the subtraction agent.

Another method for compensating for background radiation due to non-specific uptake of antibody by tumor and other tissues is to use "normal"/"irrelevant" immunoglobulin, labeled with a separately detectable label, as a subtraction agent. By "irrelevant" immunoglobulin is meant immunoglobulin which does not bind to cancer antigens or other antigens associated with the pathological lesion, and which does not substantially bind to other tissues, serum components or other substances in the body, as a result of specific antigen-antibody binding to the hypervariable/idiotypic region of the immunoglobulin. Thus, ideally, a specific antibody and an irrelevant immunoglobulin, preferably but not necessarily of the same isotype and similar secondary and tertiary structures, should have substantially comparable biodistribution except where the specific antibody forms a complex with its complementary antigen.

Suitable such irrelevant immunoglobulin subtraction agents for use with specific anti-cancer antibodies are disclosed in the Goldenberg patents, especially U.S. Pat. No. 4,348,376 and U.S. Pat. No. 4,444,744, as are suitable radionuclides that can be paired for use in this method, ways to bind such radionuclides to antibodies, and ways to introduce such agents for effective imaging. It should be understood that the present invention is not limited to particular irrelevant immunoglobulins or pairs of radionuclides. Rather, any pair of labeled specific antibody and irrelevant immunoglobulin having separately detectable labels can be used, provided that the radiolabeling is so effected that the kinetics and distribution of the radiolabeled primary antibody and indifferent immunoglobulin in the patient are substantially the same during the time period required for scanning.

Various techniques can be employed to use the differences in counts between the radionuclide label of the specific primary antibody at different sites and the relative differences in counts between the radionuclide label of the irrelevant immunoglobulin at those sites to compensate for non-specific antibody uptake. These techniques will involve elements of statistical analysis, starting with an ideal case and proceeding to the types of corrections necessary to compensate for deviations from ideality found in real intraoperative and/or endoscopy situations. It will be useful to set out an illustrative ideal case and examples of the types of correction factors which can be applied, but it should be recognized that other conventional statistical approaches can be used which are substantially equivalent.

The model case will use a specific antibody binding to a cancer antigen and labeled with I-131 (131-I-Ab), and irrelevant immunoglobulin labeled with I-123 (123-I-N). The following definitions and relationships will be used to relate the activity in normal/non-tumor tissue and the activity in tumor tissue for the ideal case:

x=131-I-Ab activity in non-tumor tissue;
y=123-I-N activity in non-tumor tissue;
A=131-I-Ab activity at putative tumor site;
B=123-I-N activity at putative tumor site.

Assuming that the amount of 131-I-Ab activity is equal to the amount of 123-I-N activity initially (or that the relative activities are normalized), and that their non-specific uptakes are the same but specific uptake of 131-I-Ab in tumor occurs, it follows that, in the ideal case:

$$x/y=1;$$

$A/B>1$ and $A/B>x/y$ at a tumor site; and that, when A and B are determined at a tumor site:

$$A/x>1;\ B/y\geq 1;\ \text{and}\ A/x\geq B/y.$$

In an ideal intraoperative or endoscopic scanning procedure, a probe able to separately detect radiation in two channels corresponding to emission from the primary antibody label and the irrelevant antibody label, respectively (assuming no scatter for the moment), is first placed over an area, preferably several areas, of normal tissue, then moved to a site of suspected tumor. The following operations are effected:

1. Confirm $x/y=1$ (deviations from ideality corrected infra);
2. Determine $A/B$ from counts in the separate detector channels;
3. When $A/B>1$ for the suspected site, it is likely that tumor tissue is present at that site.

This ideal model can easily be corrected/modified to take account of, e.g.:

Biodistribution differences of Ab and N;
Isotope scatter;
Physical decay and isotope ratio variance.

To correct for biodistribution differences, i.e., the situation where x/y departs from unity, the value of x/y in a representative number of non-tumor areas is determined, and the average value, herein denoted "r", is set as the correction factor by which A/B must be multiplied to correct for differing biodistribution of the labeled specific antibody and labeled irrelevant immunoglobulin.

To correct for isotope scatter, an empirical determination will be required, using separate samples of the individual labels. It will be difficult to correct for scatter if emissions from both labels cross over into the channel for the other label, and it is strongly preferred that substantially only one of the two radionuclides used to label the immunoglobulins, at most, crosses over into the channel for the other label. Assuming that such is the case, an empirical determination is made of the counts in each channel for a known amount of the radionuclide label that crosses over, and a correction factor, herein denoted "s", is calculated. This factor must be applied to correct individual values for x and y at a particular site before x/y is determined, and must similarly be used to correct A and B before A/B is determined.

For example, if the label on Ab shows crossover to the channel for the label on N, an empirical determination is effected using the Ab label alone, and the proportion of counts in the N channel relative to the Ab channel, s, is measured. Later readings of counts in the N channel, in the presence of both the N and the Ab label, again assuming substantially no crossover of the N label to the Ab channel, must be reduced by (s)(x) or (s)(A) counts for determinations of y or B.

To correct for physical decay and isotope ratio variance, the initial isotope activity ratio, "p", is determined, and then the rates of decay of the two labels are used to calculate the expected activity ratio at a later time, t, at which the readings are effected in normal and suspected tumor tissues. For example, if the activity of 123-I-N is 10 times the activity of 131-I-Ab at the time of injection, and a reading during surgery or endoscopic examination is made 24 hours after injection, the corrections are made as follows:

At injection, x/y=1/10.

The 123-I half-life is 13 hours and the 131-I half-life is 8 days; so that after 24 hours, only about 1/16 of the activity of 131-I is lost, whereas about ¾ of the 123-I activity is lost. The expected normal ratio, x/y, should therefore be:

(1/10)(0.918/0.25)=0.367.

Suppose the crossover of counts from the Ab channel to the N channel is 35%, and that the actual readings for x and y in a region of normal tissue are Ab channel=1000 counts (131-I);

N channel=4000 counts (123-I).

The reading in the N channel is corrected by subtracting for crossover, so that:

x=1000 counts; and
y=4000−[(1000)(0.35)]=3650 counts.
It is now seen that, at t=24 hours, x/y=1000/3650=0.277.

Absent unequal biodistribution, we expected x/y to be 0.367: therefore,
r=0.367/0.277=1.323.

The probe is then positioned over a site of suspected tumor tissue, and the process is repeated.

The readings in the Ab channel and the N channel are taken, and the 24 hour time is assumed invariant.

The reading in the N channel is corrected for crossover.

The ratio of the corrected readings in the Ab and N channels is calculated, and the biodistribution factor, r, is applied. The result, denoted A/B, is compared to x/y. If A/B is greater than x/y, then the site is considered to be a tumor tissue site.

Still more sophisticated corrections can be introduced into the model to account for other departures from ideality in actual detection situations. There will be some attenuation of signal for different thicknesses or compositions of normal and tumor tissue. Thus, several measurements of x/y for normal tissues may yield different corrected values because of unequal effects of these parameters on the two antibodies or radionuclide labels. It may be necessary to select a set of parameters from a library of such parameters determined in normal tissue, so that the various correction factors most closely approximate those for the type of tissue scanned. If the variation in the value of x/y in normal tissue is within a narrow range, it may suffice to take an average value thereof. Further minor corrections for departures from ideality of other sorts may be necessary in certain cases, but these will be readily apparent to the skilled clinician and/or nuclear medicine physician, and well within the ordinary skill of such a professional, and their inclusion is within the broad scope of the present invention.

The final processed readout from the dual channel probe can be provided to the surgeon or clinician in a variety of forms. For example, when the value for A/B at a suspected tumor site exceeds that for x/y, applying the necessary corrections as set forth above, the physician can select a level of difference which he considers significant, generally at least 15% of the normal value, preferably at least 30%, and set the probe to give an auditory or visual signal when that level is attained at any particular locus in the course of a scan.

The probe can be combined with surgical removal of detected tumor tissue, and this is the conventional mode of operation in second look surgery. Another possibility for such surgery, and especially for endoscopic procedures, is to combine the probe with a laser device that could use the signal generated by the probe to indicate where laser irradiation should be directed to selectively destroy tumor tissue.

Suitable laser devices, combined with fiber optic transmission, are well known in the art. Representative examples thereof are described, inter alia, in, e.g., Dixon, *Lasers in Surgery*, in "Current Problems in Surgery", Pgs. 1–65 (Year Book Medical Pubs., Inc. 1984); Fleisher, *Arch. Intern. Med.*, 144, 1225–1230 (1984); Wood et al., *Am. J. Gastroent.*, 80, 715–718 (1985); and Hunter et al., *Am. J. Surg.*, 148, 736–741 (1984). Three types of lasers are currently in fairly widespread use for medical therapy, namely the argon, carbon dioxide and neodymium-YAG (yttrium aluminum garnet) lasers. As noted by Fleisher, Nd-YAG and argon lasers have been used with fiber optic waveguides, although it is likely that further advances in $CO_2$ laser technology will permit its use with fiber optics in the near future.

The foregoing references show that lasers have been used for therapy, in conjunction with endoscopy, both in coagulative and in ablative modes, including their use for tumor therapy. The use of lasers and endoscopy has advantages where surgery is contraindicated. Used in conjunction with RAID in a combined endoscopic procedure according to the present invention, greater precision and mitigation of damage to normal tissue is achieved.

The use of second antibody clearance to enhance imaging of tumors and infectious lesions using an external radiation detector, e.g., a gamma camera, is disclosed in Goldenberg U.S. Pat. No. 4,624,846. This reference provides ample disclosure of types of antibodies and sources thereof for use in clearance of primary antibodies and/or their labeling moieties from the circulation to reduce background radiation and to enhance imaging.

Second antibody clearance increases the localization ratio of the labeled primary antibody in tumor tissue. It is used in the present invention to reduce non-specific background radiation. As used herein, the term "localization ratio" means the ratio of target to non-target activity of the radionuclide used to label the primary antibody. In general, the method of the invention will increase the localization ratio by at least about 20%, preferably at least about 50%, and often by a considerably higher factor, within about 2–72 hours following injection of the second antibody. Generally this is accompanied by a reduction in the level of circulating labeled primary antibody by about 10–85%, preferably by at least about 50%, and often higher, within about 2–72 hours following injection of the second antibody.

It will be understood that the second antibody used for clearance of primary antibody and/or its labeling moiety can be whole immunoglobulin or an immunoglobulin fragment, as disclosed for the related clearance method in U.S. Pat. No. 4,624,846. The administration protocols and other strategies for further enhancing localization and reducing background will be similar to those disclosed in the aforementioned reference for second antibody clearance in imaging procedures, and the skilled clinician will recognize those factors common to these two different procedures which would indicate an overlap in particular factors involved.

However, it normally will not be possible to optimize scanning in the same way for intraoperative or endoscopic examination as it is for external imaging. Rather, in the event that it is desired to optimize the timing of surgery or endoscopy, a blood sample can be taken at periodic intervals after injection of the second antibody and the level of activity of the primary antibody label in the blood is determined, so that the efficacy of clearance and the level of circulating label can be observed. This will indicate the best time for surgery or endoscopy, and/or the need for repeated injection of second antibody to further reduce the level of circulating label. For example, when the level of circulating primary antibody label is reduced by at least about 75%, preferably by at least about 85%, or even more, the interference of background radiation with the short-range tumor detection process will be minimized, and surgery will be optimal.

It is again emphasized that combinations of subtraction and second antibody clearance can be used to further enhance the efficacy of background reduction and correction for non-specific uptake of label provided by the herein disclosed aspects and embodiments of the invention, and that such combinations fall within the broad scope of the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

INTRAOPERATIVE TUMOR DETECTION

A male patient with a sigmoid colon cancer, as diagnosed by sigmoidoscopy and biopsy, is injected intravenously with I-131-labeled murine monoclonal antibody to carcinoembryonic antigen (CEA) (3 mCi I-131; 1 mg antibody immunoglobulin-G F(ab')$_2$) and irrelevant murine IgG F(ab')$_2$ labeled with I-123 (8 mCi; 1 mg IgG fragment). The patient is scanned with a gamma camera and the site or sites of tumor are imaged according to the methods of Goldenberg U.S. Pat. No. 4,331,647. At a time when the optimal differentiation of I-123 irrelevant activity from I-131 specific (tumor) activity is achieved, usually within about 24 hrs, the patient undergoes surgery for removal of the sigmoid colon cancer and any other sites in regional lymph nodes, in the liver, or elsewhere. This is achieved by passing a sterile probe over the viscera. The probe has a cadmium telluride scintillation crystal, collimator, preamplifier and amplifier, similar to that reported by Aitken et al., op. cit., but is modified to include a comparator circuit capable of selecting only the high energy I-131 band in one channel or a total gamma counts band on an alternating basis, and a derived difference readout, corrected for scatter as described hereinabove, corresponding to the I-123 counts in a second channel.

The probe signals are processed to produce a reading corresponding to the ratio of counts in the I-131 channel to those in the I-123 channel, corrected for the decay rates of the radionuclides, and normalized to unity at representative non-tumor sites. The processed readings are translated into a digital recording and an auditory signal, such that a significant increase in the ratio of gamma ray counts of specific antibody I-131 over background I-123 results in an increase in auditory pitch. An increase in counts ratio and signal of at least 15% relative to non-tumor areas is noted in this patient at the site of the sigmoid colon mass and extending to a distance of about 1.5 cm from the gross margins of the tumor. The tumor mass is surgically resected, together with a section of the sigmoid colon extending a distance of 1.5 cm from the gross margins of the tumor on all sides, at which distance the ratio of counts was not more than 5% higher than the normalized baseline ratio. Also, two mesenteric lymph nodes give at least 15% increased signals and are resected. For control purposes, six other regional lymph nodes without increased signals are also resected.

The resected tissues are fixed in formalin and are found by histopathology, except for the six lymph nodes without increased signals, to contain adenocarcinoma, classified as a Dukes' C lesion. The colon tumor borders are found to be free of cancer invasion, since these are determined by the drop of signal beyond the major tumor mass. No areas of increased signal (specific antibody radioactivity compared to control radioactivity) are found elsewhere in the abdominal cavity, including over the liver, which is the major distant site of colon cancer metastasis. Based upon follow-up of the patient up to one year after surgery, no evidence of local or distant recurrence of the cancer is found, despite repeated CT scans and laboratory tests for circulating CEA and liver function.

EXAMPLE 2

ENDOSCOPIC TUMOR DETECTION AND THERAPY (A) A man with a history of multiple polyps is admitted for colonoscopy because of a recent positive hemoccult test for the presence of blood in his stool. A dose of murine monoclonal antibody against colon cancer-associated antigen labeled with I-131, is injected i.v. (3 mCi I-131 with 0.5 mg IgG protein), and 6 hrs later, 12 mg of goat antibody against the murine monoclonal antibody (anti-antibody or second antibody) is injected to rapidly clear the nontarget (circulating and background nonspecific) radioactivity. On the next day, approximately 16 hrs after administration of second antibody, the patient undergoes colonoscopy, using a colonoscope equipped with a radiation detector capable of measuring gamma radiation emitted by the radiolabeled antibody deposition. The detector comprises a cadmium telluride scintillation crystal mounted on the tip of an optical fiber waveguide. The optical fiber is housed within a shielded tube which itself is inserted inside the colonoscope and extends to within about 4 mm of the open end thereof, the remaining length of tubing serving as a collimator. The other end of the optical fiber leads to a photomultiplier, a preamplifier and amplifier, and means to convert the resultant signal to a corresponding auditory signal.

The gastroenterologist examining the colon with the colonoscope finds six small pedunculated polyps within a distance of 30 cm from the anal verge, and two larger lesions measuring more than 1 cm in diameter. The radiation detector shows an enhanced signal only over one of the two larger polyps, this signal appearing at least five times higher than background signals or those over the other polyps. A total of 5 polyps are removed by means of loop inserted in the colonoscope, extracted through the colonoscope and processed for histopathology. It is found that all but the one having a high radioactivity signal are free of cancer cells. The affected polyp had a nodule of adenocarcinoma of about 0.3 cm diameter.

(B) In another case of colonoscopy similar to the above, a patient receives murine monoclonal antibody against colon cancer-associated antigen (labeled with I-131), followed by a single dose of rabbit antibody against the first murine anticancer antibody. A single small polyp of about 0.7 cm in diameter is found to have an increased I-131 signal. The colonoscope is equipped with a fiber optic laser used to deliver a laser dose that coagulates the entire polyp.

EXAMPLE 3

INTRAOPERATIVE CANCER DETECTION

A woman with ultrasound suspected ovarian cancer receives an i.v. injection of I-131-labeled anti-ovarian cancer murine monoclonal antibody (3 mCi I-131; 1 mg IgG F(ab')$_2$) followed 24 hrs later with 2.0 mCi Tc-99m-labeled T101 anti-T-cell monoclonal antibody (1 mg F(ab')$_2$) i.v. Within the next 24 hrs the patient undergoes laparotomy and an ovarian mass on her left side is removed.

Prior to excision, the radiation detecting probe described in Example 1 is passed over the viscera and between the organs of the abdominal and pelvic cavities. The ovarian mass indicates the highest relative activity of I-131 relative to Tc-99m, and this increased signal is evident to the surgeon by its sound. The surgeon also passes the probe throughout the cavity, and several lymph nodes clearly show activity, occasionally even higher than the tumor mass at the left ovary. This is because the T101 antibody selectively localizes in lymphatic structures, thus constituting an organ-specific agent. Where a discrete focus of activity above this lymphatic background activity is noted, as with the tumor-associated I-131 radioactivity, then the appropriate signal indicating lymph node metastasis is obtained. Of ten lymph nodes removed, the six showing an increased signal all have mucinous cystadenocarcinoma consistent with the primary ovarian tumor, and correctly identified at surgery with the radiation probe. Since the five positive lymph nodes are in a more retroperitoneal cluster of an area showing generally increased signal with the radiation probe, this area is marked for external beam radiation therapy after removal of the implicated nodes. Therefore, while the abdominal cavity is exposed, an intraoperative radiation therapy course involving the delivery of a circumscribed high dose of radiation (approximately 6,000 rads) is instituted.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method for short-range intraoperative detection of a tumor, wherein a surgical patient is injected parenterally with a radiolabeled primary antibody which specifically binds a marker produced by or associated with a tumor, the surgically exposed interior of a body cavity of said patient is scanned at close range with a radiation detection probe, and the sites of accretion of said labeled antibody are located by detecting elevated levels of radiation at said sites with said probe, the improvement comprising compensating for or reducing non-target background radiation by injecting said patient parenterally, either concurrently or sequentially, with:

(a) a contrast or subtraction agent radiolabeled with a radioisotope emitting at an energy which is separately detectable from the primary antibody label using a radiation detection probe; radiation detected from emission of the contrast or subtraction agent being used to better define the tumor, wherein:

(i) said contrast or subtraction agent comprises an organ, blood pool or interstitial fluid non-tumor-specific contrast agent, and the resultant diffuse distribution of the contrast agent is used to define the organ, blood pool or interstitial region, whereby foci of labeled primary antibody activity are enhanced and better discriminated against a background of reduced diffuse contrast agent label activity; or (ii) said contrast or subtraction agent is a dual isotope correction agent comprising irrelevant immunoglobulin from the same or different species as that used to prepare the primary antibody, the irrelevant immunoglobulin being so labeled that the kinetics and distribution of the radiolabeled primary antibody and irrelevant immunoglobulin in the patient are substantially the same during the time period required for scanning; and wherein the ratio of primary antibody label activity to irrelevant immunoglobulin label activity at a selected site is compared to said ratio at a known non-tumor site, whereby an elevated level of primary antibody label accretion due to antigen-antibody complex formation at said selected site can be discriminated;

(b) unlabeled second antibody which specifically binds the primary antibody or the labeling moiety thereof, the second antibody being injected at a time after the injection of the primary antibody sufficient to permit specific uptake of the primary antibody by a tumor in the body cavity, and in an amount sufficent to reduce the circulating level of the primary antibody label by at least about 10–85%, or to increase the localization ratio of the labeled primary antibody by at least about 20%, within about 2–72 hours following injection of the second antibody, whereby background levels of nonspecifically distributed primary antibody and/or label are reduced in the body cavity, and the sites of accretion of labeled primary antibody as well as the level of specific uptake thereof are more effectively discriminated.

2. The method of claim 1, wherein said improvement comprises injecting said patient parenterally, either concurrently or sequentially, with a contrast agent radiolabeled with a radioisotope emitting at an energy which is separately detectable from the primary antibody label using a radiation detection probe; radiation detected from emission of the contrast agent being used to better define the tumor, and wherein said contrast agent comprises an organ, blood pool or interstitial fluid non-tumor-specific contrast agent, and the resultant diffuse distribution of the contrast agent is used to define the organ, blood pool or interstitial region, whereby foci of labeled primary antibody activity are enhanced and better discriminated against a background of reduced diffuse contrast agent label activity.

3. The method of claim 2, wherein said contrast agent comprises at least one of a radiocolloid, a radiolabeled liposome, a radiolabeled soluble salt, a radiolabeled soluble protein or a radiolabeled blood cell.

4. The method of claim 1, wherein said improvement comprises injecting said patient parenterally, either concurrently or sequentially, with a subtraction agent radiolabeled with a radioisotope emitting at an energy which is separately detectable from the primary antibody label using a radiation detection probe; radiation detected from emission of the subtraction agent being used to better define the tumor, and wherein said subtraction agent is a dual isotope correction agent comprising irrelevant immunoglobulin from the same or different species as that used to prepare the primary antibody, the irrelevant immunoglobulin being so labeled that the kinetics and distribution of the radiolabeled primary antibody and irrelevant immunoglobulin in the patient are substantially the same during the time period required for scanning; and wherein the ratio of primary antibody label activity to irrelevant immunoglobulin label activity at a selected site is compared to said ratio at a known non-tumor site, whereby an elevated level of primary antibody label accretion due to antigen-antibody complex formation at said selected site can be discriminated.

5. The method of claim 1, wherein said improvement comprises injecting said patient parenterally, either concurrently or sequentially, with unlabeled second antibody which specifically binds the primary antibody or the labeling moiety thereof, the second antibody being injected at a time after the injection of the primary antibody sufficient to permit specific uptake of the primary antibody by a tumor in the body cavity, and in an amount sufficent to reduce the circulating level of the primary antibody label by at least about 10–85%, or to increase the localization ratio of the labeled primary antibody by at least about 20%, within about 2–72 hours following injection of the second antibody, whereby background levels of nonspecifically distributed primary antibody and/or label are reduced in the body cavity, and the sites of accretion of labeled primary antibody as well as the level of specific uptake thereof are more effectively discriminated.

6. The method of claim 5, wherein a blood sample is taken at periodic intervals after injection of said second antibody, the level of circulating primary antibody label activity in the blood is determined for each sample, and the time for surgery is optimized by selecting a time when the level of circulating primary antibody label activity is reduced by at least about 85%.

7. A method for short-range endoscopic tumor detection, comprising injecting an endoscopy patient parenterally with a radiolabeled primary antibody which specifically binds a marker produced by or associated with a tumor, scanning the endoscopically accessed interior of a body cavity of said patient at close range with a radiation detection probe, and locating the sites of accretion of said labeled antibody by detecting elevated levels of radiation at said sites with said probe.

8. The method of claim 7, which further comprises compensating for or reducing non-target background radiation by injecting said patient parenterally, either concurrently or sequentially, with:

(a) a contrast or subtraction agent radiolabeled with a radioisotope emitting at an energy which is separately detectable from the primary antibody label using a radiation detection probe; the radiation detected from emission of the contrast or subtraction agent being used to better define the tumor, wherein:

(i) said contrast or subtraction agent comprises an organ, blood pool or interstitial fluid non-tumor-specific contrast agent, and the resultant diffuse distribution of the contrast agent is used to define the organ, blood pool or interstitial region, whereby foci of labeled primary antibody activity are enhanced and better discriminated against a background of reduced diffuse contrast agent label activity; or (ii) said contrast or subtraction agent is a dual isotope correction agent comprising irrelevant immunoglobulin from the same or different species as that used to prepare the primary antibody, the irrelevant immunoglobulin being so labeled that the kinetics and distribution of the radiolabeled primary antibody and irrelevant immunoglobulin in the patient are substantially the same during the time period required for scanning; and wherein the ratio of primary antibody label activity to irrelevant immunoglobulin label activity at a selected site is compared to said ratio at a known non-tumor site, whereby an elevated level of primary antibody label accretion due to antigen-antibody complex formation at said selected site can be discriminated; or (b) unlabeled second antibody which specifically binds the primary antibody or the labeling moiety thereof, the second antibody being injected at a time after the injection of the primary antibody sufficient to permit specific uptake of the primary antibody by a tumor in the body cavity, and in an amount sufficient to reduce the circulating level of the primary antibody label by at least about 10–85%, or to increase the localization ratio of the labeled primary antibody by at least about 20%, within about 2–72 hours following injection of the second antibody, whereby background levels of nonspecifically distributed primary antibody and/or label are reduced in the body cavity, and the sites of accretion of labeled primary antibody as well as the level of specific uptake thereof are more effectively discriminated.

9. The method of claim 7, wherein a laser is used to remove tumor tissue at sites of elevated primary antibody label accretion.

10. The method of claim 8, wherein a laser is used to remove tumor tissue at sites of elevated primary antibody label accretion.

11. The method of claim 7, which further comprises injecting said patient parenterally, either concurrently or sequentially, with a contrast agent radiolabeled with a radioisotope emitting at an energy which is separately detectable from the primary antibody label using a radiation detection probe; radiation detected from emission of the contrast agent being used to better define the tumor, and wherein said contrast agent comprises an organ, blood pool or interstitial fluid non-tumor-specific contrast agent, and the resultant diffuse distribution of the contrast agent is used to define the organ, blood pool or interstitial region, whereby foci of labeled primary antibody activity are enhanced and better discriminated against a background of reduced diffuse contrast agent label activity.

12. The method of claim 11, wherein said contrast agent comprises at least one of a radiocolloid, a radiolabeled liposome, a radiolabeled soluble salt, a radiolabeled soluble protein or a radiolabeled blood cell.

13. The method of claim 7, which further comprises injecting said patient parenterally, either concurrently or sequentially, with a subtraction agent radiolabeled with a radioisotope emitting at an energy which is separately detectable from the primary antibody label using a radiation detection probe; radiation detected from emission of the subtraction agent being used to better define the tumor, and wherein said subtraction agent is a dual isotope correction agent comprising irrelevant immunoglobulin from the same or different species as that used to prepare the primary antibody, the irrelevant immunoglobulin being so labeled that the kinetics and distribution of the radiolabeled primary antibody and irrelevant immunoglobulin in the patient are substantially the same during the time period required for scanning; and wherein the ratio of primary antibody label activity to irrelevant immunoglobulin label activity at a selected site is compared to said ratio at a known non-tumor site, whereby an elevated level of primary antibody label accretion due to antigen-antibody complex formation at said selected site can be discriminated.

14. The method of claim 7, which further comprises injecting said patient parenterally, either concurrently or sequentially, with unlabeled second antibody which specifically binds the primary antibody or the labeling moiety thereof, the second antibody being injected at a time after the injection of the primary antibody sufficient to permit specific uptake of the primary antibody by a tumor in the body cavity, and in an amount sufficient to reduce the circulating level of the primary antibody label by at least about 10-85%, or to increase the localization ratio of the labeled primary antibody by at least about 20%, within about 2-72 hours following injection of the second antibody, whereby background levels of nonspecifically distributed primary antibody and/or label are reduced in the body cavity, and the sites of accretion of labeled primary antibody as well as the level of specific uptake thereof are more effectively discriminated.

15. The method of claim 14, wherein a blood sample is taken at periodic intervals after injection of said second antibody, the level of circulating primary antibody label activity in the blood is determined for each sample, and the time for surgery is optimized by selecting a time when the level of circulating primary antibody label activity is reduced by at least about 85%.

16. The method of claim 2, wherein said contrast agent is a radiolabeled organ- or tissue-specific antibody.

17. The method of claim 11, wherein said contrast agent is a radiolabeled organ- or tissue-specific antibody.

* * * * *

UNITED STATES PATENT AND TRADEMARK OFFICE
CERTIFICATE OF CORRECTION

PATENT NO. : 4,932,412

DATED : June 12, 1990

INVENTOR(S) : Milton D. Goldenberg

It is certified that error appears in the above-identified patent and that said Letters Patent is hereby corrected as shown below:

Column 2, line 48, after "discriminated;" insert -- or --.
Col. 16:
Claim 1, line 60, after "discriminated;" insert -- or --.

Signed and Sealed this

Twenty-second Day of September, 1992

Attest:

DOUGLAS B. COMER

*Attesting Officer*　　*Acting Commissioner of Patents and Trademarks*